(12) United States Patent
Qin et al.

(10) Patent No.: US 8,846,884 B2
(45) Date of Patent: Sep. 30, 2014

(54) METHOD FOR ENRICHMENT AND ISOLATION OF ENDOGENOUS TRANSCRIPTION FACTOR AND COMPLEXES THEREOF AND CORRESPONDING TANDEM ARRAYS OF CONCATENATED TRANSCRIPTION FACTOR RESPONSE ELEMENTS

(71) Applicants: Institute of Radiation Medicine, China Academy of Military Medical Sciences, Beijing (CN); Baylor College of Medicine, Houston, TX (US)

(72) Inventors: Jun Qin, Beijing (CN); Chen Ding, Beijing (CN); Qiongming Liu, Beijing (CN); Mingwei Liu, Beijing (CN); Wanlin Liu, Beijing (CN); Lei Song, Beijing (CN)

(73) Assignees: Baylor College of Medicine, Houston, TX (US); Institute of Radiation Medicine, China Academy of Military Medical Sciences, Beijing (CN)

( * ) Notice: Subject to any disclaimer, the term of this patent is extended or adjusted under 35 U.S.C. 154(b) by 15 days.

(21) Appl. No.: 13/730,177

(22) Filed: Dec. 28, 2012

(65) Prior Publication Data
US 2013/0225423 A1 Aug. 29, 2013

(30) Foreign Application Priority Data
Dec. 30, 2011 (CN) .......................... 2011 1 0457108

(51) Int. Cl.
| | | |
|---|---|---|
| *C07H 21/02* | (2006.01) | |
| *C12Q 1/68* | (2006.01) | |
| *G01N 33/543* | (2006.01) | |

(52) U.S. Cl.
USPC .......................... 536/23.1; 435/6.12; 436/518

(58) Field of Classification Search
USPC ........................................................ 536/23.1
See application file for complete search history.

(56) References Cited

FOREIGN PATENT DOCUMENTS

| CN | 1582340 A | 2/2005 |
| CN | 1721547 A | 1/2006 |
| WO | WO0155371 * | 8/2001 |
| WO | WO-2006012105 A1 | 2/2006 |

OTHER PUBLICATIONS

Anna Malovannaya et al.; Analysis of the Human Endogenous Coregulator Complexome; Cell, vol. 145, pp. 787-799, May 27, 2011.
SIPO Search Report of Chinese Patent Application No. 201110457108X.

* cited by examiner

*Primary Examiner* — Suryaprabha Chunduru
*Assistant Examiner* — Sahana Kaup
(74) *Attorney, Agent, or Firm* — Edwards Wildman Palmer LLP; Jeffrey D. Hsi

(57) ABSTRACT

The present invention provides a method for enrichment and isolation of endogenous transcription factors and their complexes. Also, this invention provides corresponding tandem arrays of concatenated transcription factor response elements (catTFRE). The method employs the property of transcription factors binding to sequence-specific DNA elements during regulation of gene expression. The catTFREs are designed and synthesized as concatenate dual copies of DNA response elements for various transcription factors. The DNA sequence of synthesized catTFRE is cloned to a target vector. Biotinylated catTFRE with 200 bp arms is prepared by PCR strategy. For enrichment and isolation of endogenous transcription factors and their complexes, the biotinylated catTFRE is immobilized to streptavidin-coated magnetic beads and then incubated with nuclear extract. Thereby endogenous transcription factors and their complexes are isolated from nuclear extract. Identification by mass spectrometry or other functional characterization can be further performed according to the application purposes.

1 Claim, 1 Drawing Sheet

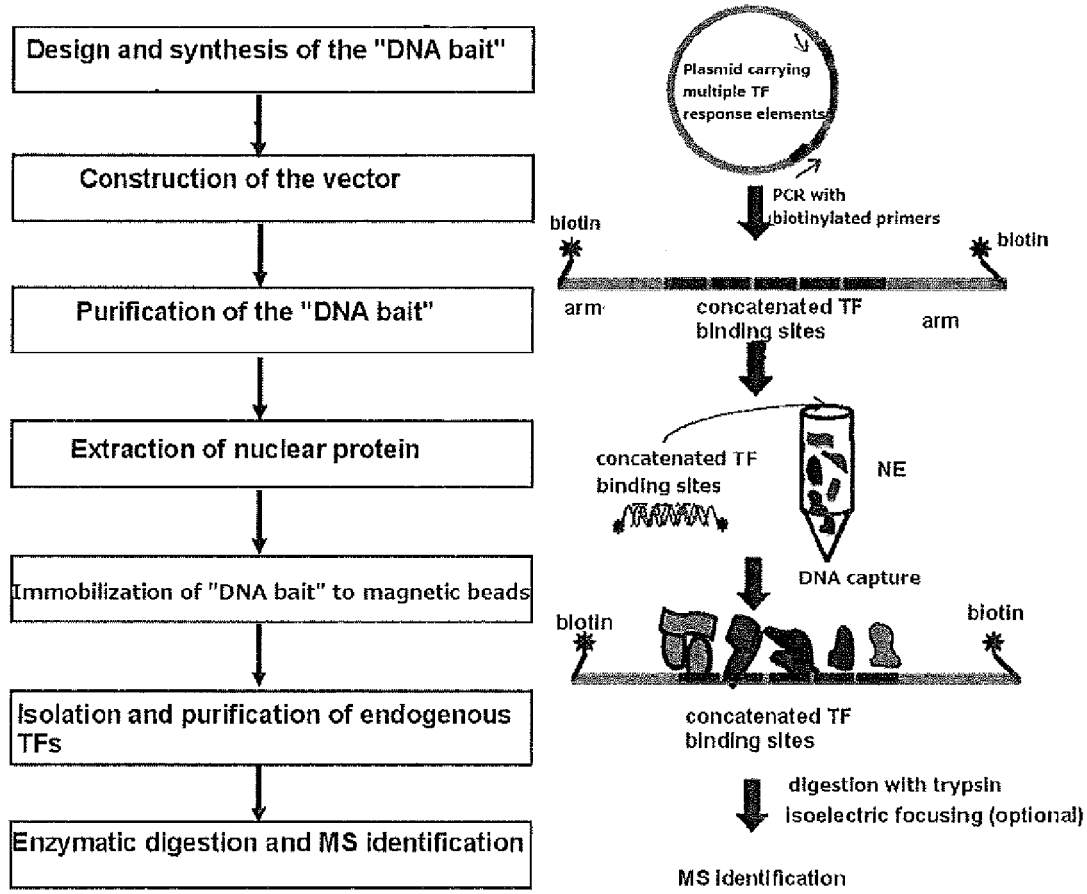

METHOD FOR ENRICHMENT AND ISOLATION OF ENDOGENOUS TRANSCRIPTION FACTOR AND COMPLEXES THEREOF AND CORRESPONDING TANDEM ARRAYS OF CONCATENATED TRANSCRIPTION FACTOR RESPONSE ELEMENTS

CROSS REFERENCE TO RELATED APPLICATIONS

This application claims priority to Chinese Application No. 201110457108.X, filed Dec. 30, 2011, the entire contents of the aforementioned applications are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 26, 2013, is named 91980(309530)_SL.txt and is 18,411 bytes in size.

TECHNICAL FIELD

This invention relates to targeting isolation and identification of a special protein group in biotechnology field. Specifically, this invention relates to the strategy for isolation and identification of organism endogenous transcription factor complexes. Also, this invention relates to the corresponding tandem arrays of concatenated transcription factor response elements (cat TFRE).

BACKGROUND

About 6% of genes in the human genome encode transcription factors (TF) which are the second largest category of proteins encoded by the human genome. Transcription factors play important roles in the regulation of gene expression and also are key nodes for intracellular signaling network, wherein, various signaling pathways triggered by intracellular and extracellular stimulations are cross linked with each other via transcription factors. Thus, transcription factors and their complexes have been attracting great concern. However, due to their low-abundance expression level (only accounting for 0.01-0.001% of total proteins within cells), it is very difficult to purify and identify transcription factors and complexes at protein level. Purification of transcription factors by a conventional chromatography method usually needs hundreds of liters of cell cultures. However, the yielded protein which has been enriched 10,000-100,000 times is barely enough for chemical and functional analysis. While antibodies are undoubtedly the best affinity reagents for detecting proteins, in fact, the commercial available antibodies with high and specific affinity to certain transcription factors are limited. Furthermore, the generation of usable antibodies for detecting endogenous proteins is a process of trial and error. Thus, applications of antibodies to affinity purification of endogenous transcription factors and their complexes are limited. To date, only less than 5% of transcription factors have been purified and identified. Therefore, a method for the purification and identification of the entire family of endogenous transcription factors is in great need.

Transcription factors regulate gene expression by binding to DNA cis-elements located in the regulatory region of target genes. Transcription factors include general transcription factors (e.g., subunits of general transcription factor II (TF II) complex, TATA-binding protein and etc.) and specific transcription factors (such as Sp1, C/EBP, AP1 and etc.). During transcription, specific transcription factors bind to promoters and general transcription factors are recruited to the DNA sequence at 40~60 base pairs upstream or downstream from the transcriptional initiation site, initiating the synthesis of RNA. Recently, more and more researches have found that structural properties of DNA binding elements will affect the formation of the transcriptional initiating complex. In other words, the nucleic acid composition of the transcription factor binding site will affect the recruitment of its co-regulators, which to a certain extent determine whether the transcription factor will act as an activator or a repressor of target genes. For this reason, it is very important to develop a method for isolation and identification of endogenous transcription factors and their complexes. The applications of such methods will shed light on the understanding of the transcriptional network of target genes.

Endogenous protein levels of transcription factors are usually very low and it is difficult to analyze the expression profile of transcription factors on proteome scale by conventional methods. To profile the endogenous transcription factors in cells or tissues, it is necessary to enrich and isolate the transcription factors by affinity purification strategy using specific reagents (such as antibodies). However, limited types of antibodies and the high cost constrained the affinity purification of endogenous transcription factors by using antibodies. In addition, only a few transcription factors can be analyzed by antibody affinity purification in a single experiment. It is hard to enrich and identify most of transcription factors expressed in certain cells or tissues by this strategy.

SUMMARY OF INVENTION

The present invention provides a method for enrichment and isolation of endogenous transcription factors and their complexes and also provides corresponding tandem arrays of concatenated concatenated transcription factor response elements (catTFRE).

The tandem arrays of catTFRE provided in this invention are DNA sequences obtained by concatenating mono or multiple copies of respective DNA response elements of one or more transcription factors with 3~5 bp nucleic acid linkers.

Specifically, the above-mentioned one or more transcription factors may be selected from the group consisting of AP1, AR, BRCA1, CEBPA, CREB1, E2F1, ELK1, ELK4, ESR1, ETS1, EWSR1-FLI1, FEV, FOXA1, FOXC1, FOXD1, FOXF2, FOXI1, FOXL1, FOXO3, Fra-1, GATA2, GATA3, GR, HIF1A::ARNT, HLF, HNF1B, HNF4A, HOXA5, INSM1, IRF1, IRF2, JunB, JunD, MAX, MEF2A, MIZF, MYC::MAX, Myf, MZF1_1-4, MZF1_5-13, NF-kappaB, NFATC2, NFE2L2, NFIC, NFL3, NFKB1, NFYA, NHLH1, NKX3-1, NR1H2::RXRA, NR2F1, NR3C1, NR4A2, Pax6, PBX1, PDX1, PLAG1, PPARG, PR, PXR-1: RXR-alpha, RAR-alpha, RAR-alpha:RXR-gam, RAR-beta: RXR-alpha, REL, RELA, REST, RFX1, RFX2, RFX3, RFX5:RFXAP:RFXANK, RORA_1, RORA_2, RREB1, RXR::RAR_DR5, RXRA::VDR, SOX10, SOX9, SP1, SPI1, SPIB, SRF, SRY, STAT1, STAT5A, T3R-beta1, TAL1:: TCF3, TBP, TEAD1, TFAP2A, TLX1::NFIC, TP53, USF1, WT1-del2, WT1-KTS, WT1I, WT1I-del2, WT1I-KTS, XBP-1, YY1 and ZNF354C.

Specifically, the tandem arrays nucleotide sequence of the catTFRE may be obtained by concatenating dual copies of respective DNA response elements of one or more transcription factors selected from AP1, AR, BRCA1, CEBPA, CREB1, E2F1, ELK1, ELK4, ESR1, ETS1, EWSR1-FLI1, FEV, FOXA1, FOXC1, FOXD1, FOXF2, FOXI1, FOXL1, FOXO3, Fra-1, GATA2, GATA3, GR, HIF1A::ARNT, HLF, HNF1B, HNF4A, HOXA5, INSM1, IRF1, IRF2, JunB, JunD, MAX, MEF2A, MIZF, MYC::MAX, Myf, MZF1_1-4, MZF1_5-13, NF-kappaB, NFATC2, NFE2L2, NFIC, NFIL3, NFKB1, NFYA, NHLH1, NKX3-1, NR1H2::RXRA, NR2F1, NR3C1, NR4A2, Pax6, PBX1, PDX1, PLAG1, PPARG, PR, PXR-1:RXR-alpha, RAR-alpha, RAR-alpha: RXR-gam, RAR-beta:RXR-alpha, REL, RELA, REST, RFX1, RFX2, RFX3, RFX5:RFXAP:RFXANK, RORA_1, RORA_2, RREB1, RXR::RAR_DR5, RXRA::VDR, SOX10, SOX9, SP1, SPI1, SPIB, SRF, SRY, STAT1, STAT5A, T3R-beta1, TAL1::TCF3, TBP, TEAD1, TFAP2A, TLX1::NFIC, TP53, USF1, WT1-del2, WT1-KTS, WT1I, WT1I-del2, WT1I-KTS, XBP-1, YY1 and ZNF354C with 3-5 bp nucleic acid linkers.

In one exemplary embodiment, the tandem arrays nucleotide sequence of the catTFRE may be obtained by concatenating dual copies of respective DNA response elements of 100 transcription factors including AP1, AR, BRCA1, CEBPA, CREB1, E2F1, ELK1, ELK4, ESR1, ETS1, EWSR1-FLI1, FEV, FOXA1, FOXC1, FOXD1, FOXF2, FOXI1, FOXL1, FOXO3, Fra-1, GATA2, GATA3, GR, HIF1A::ARNT, HLF, HINF1B, HNF4A, HOXA5, INSM1, IRF1, IRF2, JunB, JunD, MAX, MEF2A, MIZF, MYC:: MAX, Myf, MZF1_1-4, MZF1_5-13, NF-kappaB, NFATC2, NFE2L2, NFIC, NFIL3, NFKB1, NFYA, NHLH1, NKX3-1, NR1H2::RXRA, NR2F1, NR3C1, NR4A2, Pax6, PBX1, PDX1, PLAG1, PPARG, PR, PXR-1:RXR-alpha, RAR-alpha, RAR-alpha:RXR-gam, RAR-beta:RXR-alpha, REL, RELA, REST, RFX1, RFX2, RFX3, RFX5:RFXAP: RFXANK, RORA_1, RORA_2, RREB1, RXR:: RAR_DR5, RXRA::VDR, SOX10, SOX9, SP1, SPI1, SPIB, SRF, SRY, STAT1, STAT5A, T3R-beta1, TAL1::TCF3, TBP, TEAD1, TFAP2A, TLX1::NFIC, TP53, USF1, WT1-del2, WT1-KTS, WT1I, WT1I-del2, WT1I-KTS, XBP-1, YY1 and ZNF354C with 3-5 bp nucleic acid linkers.

In one specific embodiment, the tandem array nucleotide sequence of the catTFRE is represented by Seq: No: 1 in the sequence list.

Seq: No: 1 in the sequence list is consisted of 2800 base pairs, which contains dual-copies of core response elements of the above-mentioned 100 transcription factors, and each of the dual-copy core response elements is spaced from the adjacent one by three random base pairs.

The second object of the present invention is to provide a method for enrichment and isolation of endogenous transcription factors and their complexes.

The method for enrichment and isolation of endogenous transcription factors and their complexes provided in this invention comprises the steps of 1) ligating the catTFRE sequence above to the multiple cloning site of a target vector to obtain a recombinant vector carrying the catTFRE sequence;
2) designing and synthesizing a pair of primers labeled with biotin, of which the forward and reverse primers can be respectively annealed to the sequences at 200 bps upstream and downstream from the multiple cloning site of target vector, performing PCR amplification with the biotinylated primers by using the recombinant vector obtained in step 1) that carries the catTFRE sequence as the template, and purifying the biotinylated DNA (named DNA bait) produced by PCR by agarose gel electrophoresis and Minigel purification kit;
3) immobilizing the DNA bait obtained in step 2) to streptavidin-coated magnetic beads; and
4) preparing nuclear extract, incubating the magnetic beads obtained in step 3) that is immobilized with DNA bait with the nuclear extract, washing unbound proteins from beads, and then capturing endogenous transcription factors and their complexes in the nuclear extract to the solid magnetic beads by the DNA bait so as to enrich and isolate the endogenous transcription factors.

In the above-mentioned method for enrichment and isolation of endogenous transcription factors and their complexes, the target vector in step 1) may be pUC57, pET24a+, pGEX4T-2, pGEX4T-1, pCMV-Myc, pGH, pcDNA-Myc, and etc.

The nucleotide sequence of the forward primer in step 2) is represented by Seq: No: 2 in the sequence list and the nucleotide sequence of the reverse primer is represented by Seq: No: 3 in the sequence list. The PCR reaction system of 100 μl is as follows: 10× ExTaq Buffer, 10 μl; dNTPs (2.5 mM/dNTP), 10 μl; pUC57-sdTF, 1 μl (50 ng); each of forward and reverse primers, 1 μl (1 nmol); ExTaq, 0.5 μl; $H_2O$, 87.5 μl. The reaction conditions for PCR is as follows: 94° C. for 2 min at first; subsequently, 94° C. for 45 s, 60° C. for 45 s, 72° C. for 2 min, 35 cycles in total; then 72° C. for 7 min; 4° C. for 30 min at last.

The method in step 3) for immobilizing the DNA bait to the streptavidin-coated magnetic beads comprises the steps of
1) pipetting out 120 μl of magnetic beads to a clean Eppendorf tube, placing the tube on a magnetic shelf to attract the magnetic beads, and then removing the supernatant and washing the magnetic beads with 500 μl of 1×DNA Binding Buffer;
2) adding 15 pmol (278 μg) of biotin-catTFRE DNA and adjusting the binding system with 5×DNA Binding Buffer to 1×DNA Binding Buffer;
3) incubating the binding system at 4° C. for 20 min while shaking; and
4) washing the beads with BC150 twice and removing all the supernatant.

The nuclear extracts used in step 4) are extracted by employing homogenization procedure with Dounce homogenizer. Specifically, cells are suspended in a low-salt hypertonic buffer for 10 min and then homogenized to separate nuclear and cytoplasm fractions. Homogenate is spin at 4000×g for 15 min. Nuclear pellet is re-suspended with a low-salt solution and treated by Dounce for 10 times. Then, the salt concentration is adjusted to 300 mM with a high-salt solution. NE is spin down at 60,000 RPM in Ultracentrifuge (Beckman Optima TLA 100 rotor) for 20 min at 4° C. The supernatant is taken and dialyzed with BC150 solution till final salt concentration reached 150 mM. Specific procedures are as follows: cells are harvested by centrifugation at 1000×g under 4° C. for 10 min; cell pellet is washed with 1×PBS and re-suspended with a hypotonic solution at 10 times of the precipitate volume; after stayed on ice for 10 min, cells are harvested by centrifugation at 1000×g tinder 4° C. for 10 min; the cell pellet is re-suspended with a hypotonic solution of ¼ volume of that of the pellet and homogenized 15 times with a Dounce homogenizer; nuclear and cytoplasm fractions are separated by centrifugation at 4000×g under 4° C. for 15 min; the nucleus pellet is re-suspended with a low-salt buffer of ½ volume of that of nucleus and then homogenized 10 times with a Dounce homogenizer at 4° C.; the solution is transferred to a centrifugal tube; a high-salt buffer of ½ volume of that of nucleus pellet is added drop by drop while the solution is gently stirred; the solution mixture is rotated at 4° C. for 30 min and then centrifuged at 25,000×g under 4° C. for 20 min; the supernatant is dialyzed at 4° C. for 30 min in a BC150 buffer; the nuclear extract is aliquoted and quick-frozen with liquid nitrogen, and then reserved at −80° C. for future use.

For enrichment and isolation of endogenous transcription factors, 4~8 mg of nuclear extract is incubated with the magnetic beads obtained in step 3) at 4° C. for 2 hr. The unbound proteins are washed with NETN (50 mM NaCl, 0.25% NP-40) twice and then with PBS for three times, each for 10 s. By now, endogenous transcription factors and their complexes are enriched.

Depending on the purposes of application, the method above may further comprise a step of eluting the endogenous transcription factors and their complexes which bind to DNA bait immobilized on the magnetic beads. Alternatively, the method of the present invention may further contain a step of identification of endogenous transcription factors and their complexes captured by the DNA bait in step 4), which comprises steps of digesting the endogenous transcription factors and their complexes by trypsin, drying the digested peptides and identifying the components of endogenous transcription factors and their complexes by mass spectrometry. The digestion procedure is as follows: 45 μl of 50 mM $NH_4HCO_3$ (pH 8.0) is added to the magnetic beads after washing and then 10 μl of trypsin (Promega) solution (100 μg/ml) is added to digest the targets at 37° C. overnight; then 5 μl of trypsin (Promega) solution (100 μg/ml) is added again for digestion at 37° C. for 1 hour; the peptides are extracted from beads with 200 μl of 50% acetonitrile (containing 0.1% of formic acid); the mixture is shaken fiercely for 10 min and the supernatant is transferred to a clean tube; the whole mentioned procedure is repeated once. Thereafter, supernatants are combined and dried. Then, the components of endogenous transcription factors and their complexes are identified by mass spectrometry. The procedure for MS analysis is as follows: Tryptic peptides are dissolved with loading buffer (5% Methanol, 0.1% Formic acid) and then separated on an on-line C18 column (75 μm-inner diameter, 360 μm-outer diameter, 10 cm, 3 μm, C18). Mobile phase A is consisted of 0.1% formic acid in water solution and mobile phase B is consisted of 0.1% formic acid in acetonitrile solution; a linear gradient from 3 to 100% B over a 75 minute period at a flow rate of 350 nL/min is applied. For identification, peptides are fragmented by collision-induced dissociation (CID) and analyzed by the LTQ-Orbitrap Velos (Thermo, Germany). The survey scan is limited to 375-1600 m/z. Proteins are identified using the Proteome Discoverer 1.3 using MASCOT search engine and appropriate reference sequence protein database from NCBI. Threshold score/expectation value for accepting individual spectra is set to ion score 10. The PSM false positive rate is set to 1% strict/5% relaxed cutoff. The mass tolerance is set at 20 ppm for precursors and 0.5 Da for product ions. Dynamic modifications of oxidation (Met), acetylation (protein N-terminus), phosphorylation (ST) and Destreak (C) are chosen. Maximum missed cleavage sites are set to be 2.

Other methods such as Western Blotting, ELISA and etc. may, of course, be adopted to verify specific transcription factors or co-regulatory proteins as well.

The use of the catTFRE in the enrichment and isolation of endogenous transcription factors and their complexes is also contained in the present invention.

A further object of the present invention is to provide a test chip or an ELISA assay kit for detection of endogenous transcription factors or their complexes, which contains the biotinylated catTFRE as affinity reagents as mentioned above.

Hereinabove, we provide a method for enrichment and isolation of endogenous transcription factors and their complexes by employing the binding property of transcription factors to sequence-specific DNA response elements. We have surveyed the response element of various transcription factors and tandemly combined them into a concatenated tandem array of the consensus TF response element sequence. The DNA bait, biotinylated catTFRE with arms of 200 bp, is produced through molecular cloning technology. For enrichment and isolation of endogenous transcription factors and their complexes, the biotinylated DNA baits are immobilized to streptavidin-coated magnetic beads. Then the immobilized catTFRE is incubated with nuclear extract. After unbound proteins are washed away, endogenous transcription factors and their complexes are enriched and isolated. At last, identification by mass spectrometry or functional characterization of certain transcription factors by other methods can be employed according to different application purposes. The present invention further comprises the design of "DNA bait". Specifically, such a design comprises of steps of producing DNA sequence containing multiple copies of DNA response elements by strategies of de novo synthesis or in vitro ligation, ligating DNA sequence to target vector, designing and synthesizing a pair of biotin-labeled primers annealed to two ends of the multiple cloning site of the vector and then obtaining the biotinylated "DNA bait" by PCR. The 200 bp arms of DNA baits allow the formation of a spatial structure which facilitates the binding of transcription factors when the "DNA bait" is immobilized to magnetic beads. The present invention adopts the DNA binding property of transcription factors to enrich and isolate endogenous transcription factors and their complexes. Since the affinity of transcription factor to its consensus binding sites is several orders of magnitude higher than that to non-specific DNA, using DNA sequences containing consensus binding sites of transcription factors is a relatively direct method for isolation of transcription factors and associated proteins. In addition, it is easier to obtain DNA than antibodies. Furthermore, native conformations of transcription factors can be maintained upon binding to its consensus DNA element. Therefore, using DNA consensus elements to affinity purify transcription factors and their complexes has greater advantages, which provides a powerful tool for characterizing the composition of transcription factor complexes and analyzing their dynamic behaviors.

Hereinafter, the present invention will be further described in detail in conjunction with specific examples.

BRIEF DESCRIPTION OF THE DRAWINGS

FIG. 1 is a flowchart of the method for isolation and identification of endogenous transcription factors and their complexes.

DETAILED DESCRIPTION OF THE INVENTION

Examples are conducted on basis of the technical solution of the present invention and detailed embodiments and concrete procedures are provided. However, the protection scope of the present invention is not limited to the following examples.

Methods used in the following examples are all conventional methods unless otherwise indicated.

Example 1

Isolation and Identification of Transcription Factors and their Complexes in Nuclear Extract of Mouse Liver Hepatocytes Transcription factors and their complexes in nuclear extract of mouse liver hepatocytes are isolated and identified using the method of the present invention. Specifically, the method comprises the following steps as shown in FIG. 1.

1. Obtaining of catTFRE

In the example, 100 transcription factors and their DNA response elements as shown in Table 1, and tandem arrays of the catTFRE were designed and synthesized to enrich and isolate endogenous transcription factors and their complexes. The tandem arrays sequences of catTFRE were obtained by randomly concatenating dual copies of respective DNA response elements of transcription factors including AP1, AR, BRCA1, CEBPA, CREB1, E2F1, ELK1, ELK4, ESR1, ETS1, EWSR1-FLI1, FEV, FOXA1, FOXC1, FOXD1, FOXF2, FOXI1, FOXL1, FOXO3, Fra-1, GATA2, GATA3, GR, HIF1A::ARNT, HLF, HNF1B, HNF4A, HOXA5, INSM1, IRF1, IRF2, JunB, JunD, MAX, MEF2A, MIZF, MYC::MAX, Myf, MZF1_1-4, MZF1_5-13, NF-kappaB, NFATC2, NFE2L2, NFIC, NFIL3, NFKB1, NFYA, NHLH1, NKX3-1, NR1H2::RXRA, NR2F1, NR3C1, NR4A2, Pax6, PBX1, PDX1, PLAG1, PPARG, PR, PXR-1:RXR-alpha, RAR-alpha, RAR-alpha:RXR-gam, RAR-beta:RXR-alpha, REL, RELA, REST, RFX1, RFX2, RFX3, RFX5:RFXAP: RFXANK, RORA_1, RORA_2, RREB1, RXR:: RAR_DR5, RXRA::VDR, SOX10, SOX9, SP1, SPI1, SPIB, SRF, SRY, STAT1, STAT5A, T3R-beta1, TAL1::TCF3, TBP, TEAD1, TFAP2A, TLX1::NFIC, TP53, USF1, WT1-del2, WT1-KTS, WT1I, WT1I-del2, WT1I-KTS, XBP-1, YY1 and ZNF354C with linkers of 3~5 base pairs. Seq: No: 1 in the sequence list is consisted of 2800 base pairs, showing a tandem array nucleotide sequence of the catTFRE containing dual-copies of respective DNA response elements of the 100 transcription factors, having 3 base pairs between adjacent DNA response elements.

TABLE 1

Transcription factors and corresponding DNA response elements

| Transcription factors | DNA response elements |
|---|---|
| AP1 | TGACTCA |
| AR | AGAACACATTGTTCT (SEQ ID NO: 4) |
| BRCA1 | ACAACAC |
| CEBPA | TTTCGCAAT |
| CREB1 | TGACGTCA |
| E2F1 | TTTGGCGC |
| ELK1 | GAGCCGGAAG (SEQ ID NO: 5) |
| ELK4 | ACCGGAAGT |
| ESR1 | GGCCCAGGTCACCCTGACCT (SEQ ID NO: 6) |
| ETS1 | TTTCCG |
| EWSR1-FLI1 | GGAAGGAAGGAAGGAAGG (SEQ ID NO: 7) |
| FEV | CAGGAAAT |
| FOXA1 | TGTTTACTTTG (SEQ ID NO: 8) |
| FOXC1 | GGTAAGTA |

TABLE 1-continued

Transcription factors and corresponding DNA response elements

| Transcription factors | DNA response elements |
|---|---|
| FOXD1 | GTAAACAT |
| FOXF2 | CAAACGTAAACAAT (SEQ ID NO: 9) |
| FOXI1 | GGATGTTTGTTT (SEQ ID NO: 10) |
| FOXL1 | TATACATA |
| FOXO3 | TGTAAACA |
| Fra-1 | TTACTGACTCACCACAT (SEQ ID NO: 11) |
| GATA2 | GGATA |
| GATA3 | AGATAG |

2. Construction of a Recombinant Vector Carrying the catTFRE

The catTFRE obtained in step 1 was inserted into the multiple cloning site of the target vector pUC57 to get a recombinant vector carrying the catTFRE. Specific method was as follows: de novo synthesis was performed to obtain a catTFRE DNA of 2.8 kb length (Seq: No: 1 in the sequence list) and the synthesized catTFRE was inserted to the pUC57 vector by using restrictive enzymes EcoRI and HindIII. The recombinant vector was transformed and amplified in the E. coli DH5a strain, which can be used as the template of PCR for biotinylated catTFRE.

3. Preparation of Biotinylated DNA Bait

A pair of primers labeled with biotin was designed and synthesized, of which the forward and reverse primers can be annealed to sequences at 200 bps upstream and downstream from the multiple cloning site of target vector.

The nucleotide sequence of the forward primer was: 5'-CATTCAGGCTGCGCAACTGTTG-3' (Seq: ID: 2 in the sequence list).

The nucleotide sequence of the reverse primer was: 5'-GTGAGTTAGCTCACTCATTAGG-3' (Seq: ID: 3 in the sequence list).

PCR amplification was performed with biotinylated primers using the recombinant vector carrying the catTFRE obtained in step 2 as the template. PCR reaction system of 100 µl was prepared as follows: 10× ExTaq Buffer, 10 µl; dNTPs (2.5 mM/dNTP), 10 µl; pUC57-sdTF, 1 µl (about 50 ng); each of forward and reverse primers, 1 µl (1 nmol); ExTaq, 0.5 µl; H$_2$O, 87.5 µl. The reaction conditions for PCR was as follows: 94° C. for 2 min at first; subsequently, 94° C. for 45 s, 60° C. for 45 s, 72° C. for 2 min, 35 cycles in total; then 72° C. for 7 min; 4° C. for 30 min at last. The PCR product was purified with Minigel purification kit.

4. Immobilization of the Biotinylated DNA Bait to Streptavidin-Coated Magnetic Beads The biotinylated DNA bait obtained in step 3 was immobilized to streptavidin-coated magnetic beads (Dynabeads® M-280 streptavodin (Invitrogen)). Specifically, the following steps were done.

1) 120 µl slurry of magnetic beads was put into a clean Eppendorf tube and the tube was placed on a magnetic shelf which can attract the magnetic beads so as to remove the buffer;

2) The magnetic beads were washed with 500 μl of 1×DNA Binding Buffer;
3) Biotinylated catTFRE of 15 μmol (27.8 μg) was added and the binding system was adjusted to 1×DNA Binding Buffer by using 5×DNA Binding Buffer;
4) The mixture was incubated at 4° C. for 20 min with shaking;
5) The magnetic beads were washed with BC150 twice and all the supernatant was removed.

5. Enrichment and Isolation of Endogenous Transcription Factors and their Complexes Nuclear extract from mouse liver hepatocytes was extracted as follows: cells were harvested by centrifugation at 1000×g under 4° C. for 10 min; the cell pellet was washed with 1×PBS and re-suspended with a hypotonic solution (10 mM Tris-HCl pH7.3, 1.5 mM MgCl$_2$, 10 mM KCl, adding 10 mM β-ME and 1 mM PMSF before use) at 10 times of the precipitate volume; the mixture was stayed on ice for 10 min and then the cells were harvested by centrifugation at 1000×g undef 4° C. for 10 min; the cell pellet was re-suspended with a hypotonic solution of ¼ volume of that of the pellet and then homogenized 15 times with a Dounce homogenizer; nuclear and cytoplasm fractions were separated by centrifugation at 4000×g under 4° C. for 15 min; the nucleus pellet was re-suspended with a low salt buffer (20 mM Tris-HCl pH7.3, 1.5 mM MgCl$_2$, 20 mM KCl, 0.2 mM EDTA, 25% glycerol, adding 10 mM β-ME and 1 mM PMSF before use) of ½ volume of that of cells and then homogenized 10 times with a Dounce homogenizer at 4° C.; the solution was transferred to a centrifugal tube; a high salt buffer (20 mM Tris.HCl pH7.3, 1.5 mM MgCl$_2$, 1.2 M KCl, 0.2 mM EDTA, 25% glycerol, adding 10 mM β-mercaptoethanol and 0.5× Protein inhibitors before use) of ½ volume of that of the nucleus pellet was added drop by drop while the mixture was gently stirred; the solution mixture was rotated at 4° C. for 30 min and then centrifuged at 25,000×g under 4° C. for 20 min; the supernatant was dialyzed at 4° C. for 30 min in a BC150 buffer (20 mM Tris.HCl pH7.3, 0.15 mM KCl, 0.2 mM EDTA, 20% glycerol, adding 10 mM β-ME and 1 mM PMSF before use). The nuclear extract was aliquoted and quick-frozen with liquid nitrogen, which was then reserved at −80° C. for future use.

For enrichment and isolation of endogenous transcription factors, 200-800 μl of nuclear extract (4~8 mg) was centrifuged at 100,000×g under 4° C. for 20 min. The supernatant was transferred to a clean Eppendorf tube and 1 mM EDTA, 50 mM NaCl and 0.5 mmol PMSF were added. After determining its concentration by Bradford assay, the supernatant was incubated with the magnetic beads obtained in step 4 at 4° C. for 2 hr. The unbound proteins were washed away with NETN (50 mM NaCl, 0.25% NP-40) twice and then with PBS for three times, each for 10 s. By now, endogenous transcription factors and their complexes were enriched on the beads.

6. Identification of Endogenous Transcription Factors and their Complexes by Mass Spectrometry In order to evaluate the capacity of the method provided in this invention in enriching and isolating endogenous transcription factors and their complexes, mass spectrometry was used to identify the components of protein mixture captured by DNA bait. The protein mixture was firstly digested by trypsin as follows: 45 μl of 50 mM NH$_4$HCO$_3$ (pH 8.0) was added to the magnetic beads after washing, and then 10 μl of trypsin (Promega) solution (100 μg/ml) was added; digest was performed at 37° C. overnight; then 5 μl of trypsin (Promega) solution (100 μg/ml) was added again and digestion was performed at 37° C. for 1 more hour; peptides were extracted from beads with 200 ul of acetonitrile (contains 0.1% of formic acid); the supernatant was transferred to a clean tube and the extraction was repeated once; the solutions were combined and dried and then the components of protein mixture were identified by mass spectrometry. The procedure for MS analysis was as follows: Tryptic peptides were dissolved with loading buffer (5% Methanol, 0.1% Formic acid) and then separated on an on-line C18 column (75 μm inner diameter, 360 μm outer diameter, 10 cm, 3 μm C18). Mobile phase A was consisted of 0.1% formic acid in water solution and mobile phase B was consisted of 0.1% formic acid in acetonitrile solution; a linear gradient from 3 to 100% B over a 75 minute period at a flow rate of 350 nL/min was applied. For identification, peptides were fragmented by collision-induced dissociation (CID) and analyzed by the LTQ-Orbitrap Velos (Thermo, Germany). The survey scan was limited to 375-1600 m/z. Proteins were identified using the Proteome Discoverer 1.3 using MASCOT search engine and appropriate reference sequence protein database from NCBI. Threshold score/expectation value for accepting individual spectra was set to ion score 10. The PSM false positive rate was set to 1% strict/5% relaxed cutoff. The mass tolerance was set at 20 ppm for precursors and 0.5 Da for product ions. Dynamic modifications of oxidation (Met), acetylation (protein N-terminus), phosphorylation (ST) and Destreak (C) were chosen. Maximum missed cleavage sites were set to be 2.

As a result, up to 391 endogenous transcription factors (shown in Table 2) were identified from the sample in this experiment. It showed that a great amount of endogenous transcription factors were captured by catTFRE from nuclear extract of mouse liver hepatocytes. Therefore, the method of the present invention can be widely applicable for identification of endogenous transcription factors at a large scale, as well as for validation and quantification of specific transcription factors. More importantly, transcription factors, especially the superfamily of nuclear receptors, are attractive targets in current drug development, and some available drugs typically exert their potency by activating/inhibiting transcription factors. On the other hand, drugs are characterized in the complexity of mechanism and diversity of targets. Due to the property of multiple targets, practical effects of drugs are usually different from initial expectation, e.g., they may bring toxic or side effects, or, they may have some "unexpected" effects in treating other diseases. Full scanning on dynamic changes of transcription factors is especially important in research of pharmaceutical mechanism and side effects. The method of the present invention adopts catTFRE to enrich and isolate endogenous transcription factors in a large scale. The enriched transcription factors should be identified and quantified by appropriate methods. Using this approach, it is possible to analyze the dynamic endogenous transcription factors stimulated by certain drugs, which would provide some clues for 1) the targets of the drugs and its pharmacological mechanism; and 2) candidate targets of the drugs and the corresponding potential side effects.

It's important to note that DNA response elements of a certain transcription factor can usually enrich multiple members of a transcription factor superfamily, since members belonging to a transcription factor superfamily usually bind similar DNA sequences. For example, the nuclear receptor superfamily (48 members in human) tends to bind DNA elements containing a consensus half site with the sequence of AGGTCA. The above-mentioned reasons may account for the phenomenon that the number of transcription factors, 391, as detected in the liver in the experiment above is higher than the number of transcription factors to be enriched by catTFRE as designed.

In addition to the application to profile endogenous transcription, factors in biological organisms, tissues or cells, the catTFRE provided in this invention can also be used to develop assay kits or chips for screening endogenous transcription factors. For example, an ELISA assay kit or a test chip for detection of endogenous transcription factors can be developed by coating binding elements to a 96-well plate or on the surface of a solid substrate.

TABLE 2

Endogenous transcription factors enriched and isolated by catTFRE

| TF | SPC | TF | SPC | TF | SPC |
|---|---|---|---|---|---|
| ADNP | 11 | IRF5 | 16 | SFPI1 | 6 |
| AHCTF1 | 20 | IRF6 | 12 | SIM2 | 1 |
| AHR | 3 | IRF8 | 6 | SIX4 | 2 |
| ARID1A | 45 | IRF9 | 16 | SIX5 | 1 |
| ARID1B | 34 | JAZF1 | 2 | SKOR1 | 1 |
| ARID2 | 11 | JUN | 9 | SMAD2 | 15 |
| ARID5B | 34 | JUNB | 8 | SMAD4 | 3 |
| ARNT | 10 | JUND | 41 | SMAD5 | 3 |
| ARNTL | 301 | KLF12 | 6 | SMARCA1 | 41 |
| ARNTL2 | 3 | KLF13 | 6 | SMARCA5 | 261 |
| ASCL1 | 5 | KLF15 | 3 | SMARCC1 | 60 |
| ATF1 | 87 | KLF3 | 3 | SMARCC2 | 228 |
| ATF2 | 30 | KLF9 | 7 | SMARCE1 | 79 |
| ATF7 | 63 | LIN28B | 1 | SOX13 | 4 |
| ATOH1 | 1 | MAFB | 8 | SOX18 | 7 |
| AW146020 | 1 | MAFG | 45 | SOX5 | 23 |
| BACH1 | 39 | MAFK | 20 | SOX6 | 14 |
| BACH2 | 7 | MAX | 120 | SOX8 | 6 |
| BARHL2 | 4 | MAZ | 22 | SP1 | 13 |
| BAZ2A | 9 | MEF2C | 24 | SP3 | 21 |
| BAZ2B | 57 | MEF2D | 24 | SREBF1 | 4 |
| BBX | 2 | MGA | 29 | SREBF2 | 2 |
| BCL11B | 1 | MIER1 | 5 | SRF | 14 |
| BCL6 | 5 | MITF | 1 | SSRP1 | 55 |
| BHLHE40 | 48 | MLX | 372 | STAT1 | 636 |
| BHLHE41 | 3 | MLXIP | 8 | STAT2 | 19 |
| BPTF | 2 | MLXIPL | 438 | STAT3 | 1379 |
| BZW1 | 8 | MNT | 34 | STAT5A | 35 |
| C130039O16RIK | 12 | MTA1 | 11 | STAT5B | 39 |
| CARHSP1 | 5 | MTA2 | 108 | STAT6 | 6 |
| CASZ1 | 1 | MTA3 | 9 | TADA2B | 1 |
| CBFB | 7 | MXD1 | 2 | TBP | 34 |
| CDC5L | 16 | MXD4 | 1 | TBX3 | 18 |
| CEBPA | 56 | MXI1 | 1 | TBX5 | 1 |
| CEBPB | 73 | MYBL1 | 8 | TCF7 | 37 |
| CEBPG | 17 | MYCN | 32 | TCF7L1 | 22 |
| CEBPZ | 34 | MYT1L | 4 | TCF7L2 | 43 |
| CHD7 | 44 | MZF1 | 1 | TCFAP4 | 25 |
| CIC | 4 | NFAT5 | 32 | TCFCP2 | 102 |
| CL°CK | 281 | NFATC1 | 81 | TCFCP2L1 | 10 |
| CREB1 | 130 | NFATC2 | 7 | TCFEC | 3 |
| CREB3L3 | 20 | NFATC3 | 56 | TEAD1 | 14 |
| CREBL2 | 6 | NFE2L1 | 5 | TEAD3 | 18 |
| CREM | 73 | NFE2L2 | 1 | TEAD4 | 1 |
| CSDA | 287 | NFIA | 465 | TERF2 | 1 |
| CSDE1 | 8 | NFIB | 514 | TFAM | 512 |
| CTCF | 145 | NFIC | 482 | TFDP1 | 10 |
| CTCFL | 1 | NFIL3 | 89 | TFDP2 | 9 |
| CUX1 | 17 | NFIX | 706 | THRA | 6 |
| DBP | 2 | NFKB1 | 230 | THRB | 93 |
| DEAF1 | 4 | NFKB2 | 88 | TOX4 | 30 |
| DMAP1 | 10 | NFKBIL1 | 3 | TSHZ1 | 1 |
| DR1 | 5 | NFRKB | 82 | TSHZ3 | 1 |
| DRAP1 | 38 | NFYA | 64 | TTF1 | 15 |
| E2F1 | 1 | NFYB | 26 | TMLP1 | 2 |
| E2F3 | 43 | NFYC | 110 | UBP1 | 404 |
| E2F4 | 18 | NKX2-2 | 1 | UBTF | 717 |
| E4F1 | 1 | N°C3L | 14 | USF1 | 114 |
| EGR3 | 2 | N°C4L | 5 | USF2 | 115 |
| ELF1 | 30 | NOTCH1 | 1 | VEZF1 | 47 |
| ELF2 | 29 | NOTCH2 | 2 | WIZ | 1 |
| ELF3 | 3 | NPAS2 | 8 | XBP1 | 20 |
| ELF4 | 8 | NR0B2 | 1 | YBX1 | 989 |
| ELK3 | 20 | NR1D2 | 34 | YEATS4 | 3 |
| ELK4 | 26 | NR1H2 | 39 | YY1 | 68 |
| EP400 | 21 | NR1H3 | 104 | YY2 | 3 |
| ERF | 25 | NR1H4 | 179 | ZBTB17 | 8 |
| ERG | 42 | NR1I2 | 26 | ZBTB2 | 5 |
| ESRRA | 210 | NR1I3 | 130 | ZBTB20 | 400 |
| ESRRB | 11 | NR2C1 | 11 | ZBTB40 | 1 |
| ESRRG | 69 | NR2C2 | 124 | ZBTB43 | 6 |
| ETS1 | 3 | NR2F1 | 69 | ZBTB44 | 9 |
| ETV3 | 1 | NR2F2 | 153 | ZBTB7A | 22 |
| ETV6 | 25 | NR2F6 | 204 | ZBTB7B | 16 |
| FAM171B | 2 | NR3C1 | 119 | ZDHHC17 | 2 |
| FEZF1 | 1 | NR3C2 | 25 | ZFHX3 | 19 |
| FLI1 | 21 | NR4A2 | 31 | ZFHX4 | 13 |
| FOSL2 | 3 | NR4A3 | 12 | ZFP143 | 1 |
| FOXA1 | 24 | NR5A2 | 5 | ZFP148 | 40 |
| FOXA2 | 24 | NRF1 | 159 | ZFP184 | 1 |
| FOXA3 | 12 | ONECUT1 | 92 | ZFP187 | 5 |
| FOXF1A | 2 | ONECUT2 | 57 | ZFP189 | 1 |
| FOXJ2 | 3 | ONECUT3 | 12 | ZFP191 | 2 |
| FOXJ3 | 16 | PDX1 | 10 | ZFP219 | 11 |
| FOXK1 | 151 | PDX2 | 16 | ZFP260 | 1 |
| FOXK2 | 16 | PDX3 | 6 | ZFP263 | 4 |
| FOXN3 | 7 | PDS5B | 102 | ZFP280B | 1 |
| FOXO1 | 30 | PHOX2B | 6 | ZFP281 | 11 |
| FOXO3 | 21 | PKNOX1 | 2 | ZFP319 | 4 |
| FOXO4 | 23 | PLAGL1 | 1 | ZFP362 | 3 |
| FOXO6 | 11 | PLAGL2 | 6 | ZFP367 | 2 |
| FOXP1 | 117 | POU2F1 | 17 | ZFP382 | 1 |
| FOXP2 | 2 | POU5F1 | 1 | ZFP384 | 10 |
| FOXP4 | 48 | PPARA | 201 | ZFP42 | 4 |
| FOXQ1 | 2 | PPARD | 7 | ZFP445 | 1 |
| FOXS1 | 2 | PPARG | 29 | ZFP458 | 4 |
| GABPA | 129 | PRDM1 | 2 | ZFP462 | 1 |
| GATA4 | 12 | PRDM10 | 18 | ZFP512 | 27 |
| GATA6 | 1 | PRDM15 | 1 | ZFP516 | 1 |
| GATAD2A | 38 | PRDM16 | 18 | ZFP524 | 5 |
| GATAD2B | 22 | PROX1 | 224 | ZFP536 | 3 |
| GCFC1 | 35 | RARA | 144 | ZFP558 | 2 |
| GLI1 | 5 | RARB | 82 | ZFP574 | 1 |
| GLI3 | 1 | RARG | 111 | ZFP592 | 9 |
| GM1862 | 3 | RB1 | 13 | ZFP628 | 1 |
| GMEB1 | 10 | RBL1 | 18 | ZFP629 | 1 |
| GMEB2 | 4 | RBL2 | 51 | ZFP641 | 1 |
| HAND2 | 1 | RBPJ | 58 | ZFP644 | 1 |
| HES1 | 5 | REL | 28 | ZFP652 | 8 |
| HHEX | 14 | RELA | 94 | ZFP655 | 1 |
| HINFP | 1 | RELB | 5 | ZFP687 | 5 |
| HIVEP2 | 1 | REPIN1 | 6 | ZFP771 | 8 |
| HLX | 1 | REST | 10 | ZFP775 | 2 |
| HMBOX1 | 8 | RFX1 | 62 | ZFP777 | 1 |
| HMG20A | 34 | RFX2 | 12 | ZFP787 | 1 |
| HMG20B | 12 | RFX3 | 8 | ZFP800 | 18 |
| HMGA1 | 106 | RFX5 | 13 | ZFP819 | 1 |
| HMGA2 | 48 | RFX7 | 1 | ZFP825 | 2 |
| HMGB2 | 89 | RFXANK | 4 | ZFP827 | 1 |
| HMGB3 | 87 | RLF | 1 | ZFP828 | 4 |
| HNF1A | 445 | RORA | 4 | ZFPM1 | 8 |
| HNF1B | 53 | RORC | 20 | ZHX1 | 11 |
| HNF4A | 631 | RREB1 | 132 | ZHX2 | 19 |
| HNF4G | 7 | RUNX1 | 4 | ZHX3 | 18 |
| HSF4 | 10 | RUNX3 | 2 | ZIC3 | 1 |
| IKZF1 | 6 | RXRA | 809 | ZKSCAN1 | 2 |
| IKZF5 | 1 | RXRB | 410 | ZKSCAN14 | 4 |
| IRF1 | 5 | RXRG | 160 | ZKSCAN3 | 3 |
| IRF2 | 88 | SALL1 | 10 | ZNF512B | 1 |
| IRF3 | 59 | SATB2 | 2 | ZSCAN2 | 2 |
| IRF5 | 16 | | | ZZZ3 | 1 |

We claim:

1. A tandem array of concatenated transcription factor response elements (catTFRE), comprising the sequence of SEQ ID No: 1.

* * * * *

SEQUENCE LISTING

<160> NUMBER OF SEQ ID NOS: 61

<210> SEQ ID NO 1
<211> LENGTH: 2800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| tgactcatca | tgactcatca | acaacactca | acaacactca | tttcgcaatt | catttcgcaa | 60 |
| ttcatgacgt | catcatgacg | tcatcatttg | gcgctcattt | ggcgctcaga | gccggaagtc | 120 |
| agagccggaa | gtcaaccgga | agttcaaccg | gaagttcagg | cccaggtcac | cctgaccttc | 180 |
| aggcccaggt | caccctgacc | ttcatttccg | tttccgtcag | gaaggaagga | aggaaggtca | 240 |
| ggaaggaagg | aaggaaggtc | acaggaaatt | cacaggaaat | tcatgtttac | tttgtcatgt | 300 |
| ttactttgtc | aggtaagtat | caggtaagta | tcagtaaaca | ttcagtaaac | attcacaaac | 360 |
| gtaaacaatt | cacaaacgta | aacaattcag | gatgtttgtt | ttcaggatgt | ttgttttcat | 420 |
| atacatatca | tatacatatc | atgtaaacat | catgtaaaca | tcaggatatc | aggatatcaa | 480 |
| gatagtcaag | atagtcagga | cgtgctcagg | acgtgctcag | gttacgtaat | gtcaggttac | 540 |
| gtaatgtcat | taatatttaa | ctcattaata | tttaactcaa | ggccaaaggt | catcaaggcc | 600 |
| aaaggtcatc | acactaattt | cacactaatt | tcatgtcagg | gggcgtcatg | tcagggggcg | 660 |
| tcagaaagtg | aaacctcaga | agtgaaaacc | tcaggaaagt | gaaagcaaaa | ctcaggaaag | 720 |
| tgaaagcaaa | actcagacca | cgttatcaga | ccacgttatc | actatttata | gtcactattt | 780 |
| atagtcataa | cgtccgctca | taacgtccgc | tcagagcacg | tggttcagag | cacgtggttc | 840 |
| acagcagctg | ctgtcacagc | agctgctgtc | atggggatca | tggggatcag | taggggaat | 900 |
| cagtaggggg | aatcattttc | catcattttc | catcaatgac | tcagcatcaa | tgactcagca | 960 |
| tcattggcat | cattggcatc | attatgtaac | gttcattatg | taacgttcag | ggaatttcct | 1020 |
| cagggaattt | cctcagggga | ttcccctcag | gggattcccc | tcaaccagcc | aatcagcgtc | 1080 |
| aaccagccaa | tcagcgtcac | gcagctgcgt | tcacgcagct | gcgttcaata | cttatcaata | 1140 |
| cttatcaaaa | ggtcaaaggt | caactcaaaa | ggtcaaaggt | caactcatga | cctttgaacc | 1200 |
| ttcatgacct | ttgaaccttc | agggaacatt | atgtcctgtt | cagggaacat | tatgtcctgt | 1260 |
| tcaaaggtca | ctcaaaggtc | actcattcac | gcatgagttt | cattcacgca | tgagtttcac | 1320 |
| catcaatcaa | atcaccatca | atcaaatcac | taatttcact | aatttcaggg | gcccaagggg | 1380 |
| gtcaggggcc | caaggggtc | agtaggtcac | ggtgacctac | ttcagtaggt | cacggtgacc | 1440 |
| tacttcaggg | gatttcctca | ggggatttcc | tcagggaatt | tcctcaggga | atttcctcat | 1500 |
| tcagcaccat | ggacagcgcc | tcattcagca | ccatggacag | cgcctcaatc | aaggtcatca | 1560 |
| atcaaggtca | tcatataagt | aggtcaatca | tataagtagg | tcaatcaccc | caaaccaccc | 1620 |
| acaaccatca | ccccaaacca | cccacaacca | tcaaggtcat | ggagaggtca | tcaaggtcat | 1680 |
| ggagaggtca | tcagggtcat | cgggttcatc | agggtcatcg | ggttcatcac | tttgttcact | 1740 |
| ttgttcagaa | caatggtcag | aacaatggtc | accccgcccc | ctcacccgc | ccctcaagg | 1800 |
| aagttcaagg | aagttcaaga | ggaatcaaga | ggaatcagcc | catatatggt | cagcccatat | 1860 |
| atggtcagta | aacaattcag | taaacaattc | acatttcccg | gaaacctcac | atttcccgga | 1920 |
| aacctcacca | ccatctggtt | caccaccatc | tggttcagta | taaaaggcgg | ggtcagtata | 1980 |

```
aaaggcgggg tcacacattc ctccgtcaca cattcctccg tcagccttgg gctcagcctt    2040
gggctcatgg caccatgcca atcatggcac catgccaatc accggacatg cccgggcatg    2100
ttcaccggac atgcccgggc atgttcacac gtggtcacac gtggtcagcc atctcagcca    2160
tctcaatcca ctcaatccac tcaagaacac attgttcttc aagaacacat tgttctgtct    2220
tactgactca ccacatgtcc cccttttctga ctcacgtcca cacacacaca caaccagtcc    2280
acacacacac acaaccagtc atgacggtca tgacggtcat ttatcagaaa tggcacgtca    2340
tttatcagaa atggcacgtc ttaccagaaa agggtcccag tttcttctaa gaaggtctca    2400
ccaccggtct caccaccggt ccacgtgggc cgtccacgtg ggccgtcgta gacagacaac    2460
agtcgtagac agacaacagt ccttcaccca gcaacagatg aggcgtcctt cacccagcaa    2520
cagatgaggc gtctccactg agcccgtctc cactgagccc gtctggaagg gcagacccag    2580
gacactctca ccagtctgaa ctaagtctga actaagtcta ctgactcacc acatgtcccc    2640
ctttctgact cacgtccagt ttcggtttcc ctttgtcaaa ctccaccccc acgtcaaact    2700 ccaccccccac gtcgcacgcc agcgtcgcac gccagcgtca ataaaatag tcaataaaaa    2760 tagtccgatt cccggaaag tcccagtttc ttctaagaag                          2800
```

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cattcaggct gcgcaactgt tg                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtgagttagc tcactcatta gg                                              22

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agaacacatt gttct                                                      15

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gagccggaag                                                            10

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcccaggtc accctgacct                                                    20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggaaggaagg aaggaagg                                                      18

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgtttacttt g                                                             11

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caaacgtaaa caat                                                          14

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggatgtttgt tt                                                            12

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttactgactc accacat                                                       17

```
<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agaacacatt gttct                                                    15

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggttacgtaa tg                                                       12

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttaatattta ac                                                       12

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aggccaaagg tca                                                      13

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgtcaggggg cg                                                       12

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaaagtgaaa cc                                                       12
```

```
<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaaagtgaa agcaaaac                                                 18

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttactgactc accacat                                                  17

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cccctttctg actcac                                                   16

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaccacgtta                                                          10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctatttatag                                                          10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
taacgtccgc                                                          10

<210> SEQ ID NO 24
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gagcacgtgg t                                                          11

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagcagctgc tg                                                         12

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtaggggaa                                                             10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gggaatttcc                                                            10

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atgactcagc a                                                          11

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttatgtaacg t                                                          11

<210> SEQ ID NO 30
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 gggattccc c                                                              11

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
accagccaat cagcg                                                         15

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgcagctgcg t                                                             11

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaaggtcaaa ggtcaac                                                       17

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgacctttga acct                                                          14

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gggaacatta tgtcctgt                                                      18

<210> SEQ ID NO 36
<211> LENGTH: 14
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 36
ttcacgcatg agtt                                                    14

<210> SEQ ID NO 37
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccatcaatca aa                                                      12

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggggcccaag gggg                                                    14

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtaggtcacg gtgacctact                                              20

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agaacacatt gttct                                                   15

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tggaagggca gacccaggac actctcacca                                   30

<210> SEQ ID NO 42
<211> LENGTH: 12
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 42
tccactgagc cc                                                              12

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggggatttcc                                                                 10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gggaatttcc                                                                 10

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttcagcacca tggacagcgc c                                                    21

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cttcacccag caacagatga ggc                                                  23

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atcaaggtca                                                                 10

<210> SEQ ID NO 48
<211> LENGTH: 14
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 48
tataagtagg tcaa                                                          14

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccccaaacca cccacaacca                                                    20

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aggtcatgga gaggtca                                                       17

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gggtcatcgg gttca                                                         15

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ccccgccccc                                                               10

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcccatatat gg                                                            12

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 54
catttcccgg aaacc                                                        15

<210> SEQ ID NO 55
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttaccagaaa agg                                                          13

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccaccatctg gt                                                           12

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gtataaaagg cgggg                                                        15

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cacattcctc cg                                                           12

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tggcaccatg ccaa                                                         14

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 60
ccggacatgc ccgggcatgt                                              20

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cacacacaca cacaacca                                                18
```